(12) United States Patent
Uemoto et al.

(10) Patent No.: US 9,966,226 B2
(45) Date of Patent: *May 8, 2018

(54) CROSS-SECTION PROCESSING AND OBSERVATION METHOD AND CROSS-SECTION PROCESSING AND OBSERVATION APPARATUS

(71) Applicant: HITACHI HIGH-TECH SCIENCE CORPORATION, Minato-ku, Tokyo (JP)

(72) Inventors: Atsushi Uemoto, Tokyo (JP); Xin Man, Tokyo (JP); Tatsuya Asahata, Tokyo (JP)

(73) Assignee: HITACHI HIGH-TECH SCIENCE CORPORATION (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/728,004

(22) Filed: Jun. 2, 2015

(65) Prior Publication Data

US 2015/0262788 A1    Sep. 17, 2015

Related U.S. Application Data

(63) Continuation of application No. 14/078,852, filed on Nov. 13, 2013, now Pat. No. 9,080,945.

(30) Foreign Application Priority Data

Nov. 15, 2012 (JP) .................................. 2012-251589
Nov. 1, 2013 (JP) .................................. 2013-228112

(51) Int. Cl.
*G01N 23/225* (2006.01)
*H01J 37/304* (2006.01)
(Continued)

(52) U.S. Cl.
CPC ............ *H01J 37/265* (2013.01); *G01N 23/04* (2013.01); *G01N 23/225* (2013.01);
(Continued)

(58) Field of Classification Search
CPC ............ G01N 23/225; G01N 23/2251; G01N 23/2252; H01J 37/26; H01J 37/3053; H01J 37/3045; H01J 2237/31745
See application file for complete search history.

(56) References Cited

U.S. PATENT DOCUMENTS

| 6,583,413 B1 | 6/2003 | Shinada et al. | 850/9 |
| 6,759,655 B2 | 7/2004 | Nara et al. | 850/9 |

(Continued)

FOREIGN PATENT DOCUMENTS

| JP | 7013497 | 5/1995 |
| JP | 10055774 | 2/1998 |

(Continued)

*Primary Examiner* — Jason McCormack
*Assistant Examiner* — Sean Luck
(74) *Attorney, Agent, or Firm* — Bruce L. Adams

(57) ABSTRACT

A cross-section processing and observation method performed by a cross-section processing and observation apparatus comprises a cross-section processing step of forming a cross-section by irradiating a sample with an ion beam; a cross-section observation step of obtaining an observation image of the cross-section by irradiating the cross-section with an electron beam; and repeating the cross-section processing step and the cross-section observation step so as to obtain observation images of a plurality of cross-sections. In a case where Energy Dispersive X-ray Spectrometry (EDS) measurement of the cross-section is performed and an X-ray of a specified material or of a non-specified material that is different from a pre-specified material is detected, an irradiation condition of the ion beam is changed so as to obtain observation images of a plurality of cross-sections of (Continued)

the specified material, and the cross-section processing and observation of the specified material is performed.

6 Claims, 11 Drawing Sheets

(51) Int. Cl.
    *H01J 37/26*     (2006.01)
    *H01J 37/30*     (2006.01)
    *G01N 23/22*     (2018.01)
    *G01N 23/04*     (2018.01)
    *G01T 1/36*     (2006.01)
    *H01J 37/28*     (2006.01)
    *G01N 1/32*     (2006.01)

(52) U.S. Cl.
    CPC ..... *G01N 23/2208* (2013.01); *G01N 23/2251* (2013.01); *G01N 23/2255* (2013.01); *G01T 1/36* (2013.01); *H01J 37/28* (2013.01); *H01J 37/304* (2013.01); *H01J 37/3005* (2013.01); *H01J 37/3045* (2013.01); *G01N 1/32* (2013.01); *H01J 2237/2611* (2013.01); *H01J 2237/28* (2013.01); *H01J 2237/2807* (2013.01); *H01J 2237/2812* (2013.01); *H01J 2237/30472* (2013.01); *H01J 2237/30483* (2013.01); *H01J 2237/31745* (2013.01); *H01J 2237/31749* (2013.01)

(56) References Cited

U.S. PATENT DOCUMENTS

| | | | |
|---|---|---|---|
| 6,870,169 B2 | 3/2005 | Obara et al. | 250/492.2 |
| 7,696,487 B2 | 4/2010 | Hayakawa et al. | 250/397 |
| 8,168,950 B2 | 5/2012 | Furuhashi et al. | 250/310 |
| 2004/0126909 A1 | 7/2004 | Obara et al. | 438/14 |
| 2004/0183012 A1* | 9/2004 | Yaguchi | G01N 23/20 |
| | | | 250/306 |
| 2009/0084953 A1 | 4/2009 | Harada et al. | 250/307 |
| 2009/0242759 A1 | 10/2009 | Bray et al. | 250/307 |
| 2011/0240852 A1 | 10/2011 | Tanner | 250/307 |
| 2011/0278452 A1 | 11/2011 | Nozoe et al. | 250/307 |
| 2012/0212583 A1 | 8/2012 | Yaguchi et al. | 348/46 |
| 2012/0235055 A1 | 9/2012 | Madokoro et al. | 250/398 |
| 2013/0248708 A1 | 9/2013 | Man | 250/307 |
| 2014/0076717 A1 | 3/2014 | Nanri et al. | |

FOREIGN PATENT DOCUMENTS

| | | |
|---|---|---|
| JP | 2004191187 | 7/2004 |
| JP | 2004349118 | 12/2004 |
| JP | 2008270073 | 11/2008 |
| JP | 2011185845 | 9/2011 |
| JP | 2011187185 | 9/2011 |
| WO | 2011070727 | 6/2011 |
| WO | 2012169323 | 12/2012 |

* cited by examiner

CROSS-SECTION PROCESSING AND OBSERVATION METHOD AND CROSS-SECTION PROCESSING AND OBSERVATION APPARATUS

CROSS-REFERENCE TO RELATED APPLICATIONS

This application claims priority from Japanese Patent Application No. 2012-251589 filed on Nov. 15, 2012, and Japanese Patent Application No. 2013-228112 filed on Nov. 1, 2013, the entire contents of which are incorporated herein by reference.

TECHNICAL FIELD

Aspects of the present invention relate to cross-section processing and observation in which a cross-section formed by an ion beam is observed by an electron microscope.

BACKGROUND

As an analysis method of an internal structure or a defect of a semiconductor device or the like, a cross-section processing and observation method of performing cross-section processing of a sample with a focused ion beam, exposing a cross-section including a desirable structure or a defect, and observing the cross-section with a scanning electron microscope, has been known. According to this method, since a desirable observation target in the sample can be exposed pinpointedly, it is possible to rapidly observe the structure or the defect.

In addition, a method of repeatedly performing cross-section processing and cross-section observation, and constructing a three-dimensional image of an area which is subjected to cross-section processing by combining the plurality of obtained cross-section observation images has been known (see JP-A-2008-270073). According to this method, it is possible to construct the three-dimensional image of the observation target.

SUMMARY

In recent years, since a device pattern has become minute due to density growth or reduction in size of a semiconductor device, cross-section observation of a minute observation target is required. In order to perform cross-section processing and observation and analysis of a sample including a minute observation target, it is necessary to make slice intervals of the cross-section processing to be smaller and a number of cross-sections to be larger.

However, since the cross-section observation takes time in a cross-section processing and observation process, if the number of the cross-sections increases, there is a problem that the total time necessary for the step increases.

The present invention is made in consideration of these circumstances and an object thereof is to provide a cross-section processing and observation method with high throughput even for a sample including a minute observation target.

In order to achieve the object described above, in the present invention, cross-section processing and observation is performed with respect to a sample including a minute observation target at constant slice intervals from the front of the observation target. In this cross-section observation, in a case where EDS measurement is performed and a material of the observation target is detected, the cross-section processing and observation of the observation target is performed by setting the slice interval smaller. Accordingly, even when the observation target is smaller than the constant slice interval, it is possible to efficiently obtain a cross-section which is sufficient for analysis of the observation target.

The material of the observation target may be a material specified in advance, or an unspecified material other than the material specified in advance.

According to an aspect of the present invention, there is provided a cross-section processing and observation method performed by a cross-section processing and observation apparatus, the method including: a cross-section processing step of forming cross-section by irradiating a sample with an ion beam; cross-section observation step of obtaining an observation image of the cross-section by irradiating the cross-section with an electron beam; and repeating the cross-section processing step and the cross-section observation step so as to obtain observation images of a plurality of cross-sections formed substantially parallel with each other at predetermined intervals, wherein, in a case where Energy Dispersive X-ray Spectrometry (EDS) measurement of the cross-section is performed and an X-ray of a specified material is detected, an irradiation condition of the ion beam is changed so as to obtain observation images of a plurality of cross-sections of the specified material, and the cross-section processing and observation of the specified material is performed.

According to another aspect of the present invention, there is provided a cross-section processing and observation method performed by a cross-section processing and observation apparatus, the method including: a cross-section processing step of forming a cross-section by irradiating a sample with an ion beam; a cross-section observation step of obtaining an observation image of the cross-section by irradiating the cross-section with an electron beam; and repeating the cross-section processing step and the cross-section observation step so as to obtain observation images of a plurality of cross-sections formed substantially parallel with each other at predetermined intervals, wherein, in a case where Energy Dispersive X-ray Spectrometry (EDS) measurement of the cross-section is performed and an X-ray of an unspecified material other than a material which is specified in advance is detected, an irradiation condition of the ion beam is changed so as to obtain observation images of the plurality of cross-sections of the unspecified material, and the cross-section processing and observation of the unspecified material is performed.

According to another aspect of the present invention, there is provided a cross-section processing and observation apparatus including: a sample stage configured to place a sample thereon; an ion beam column configured to irradiate the sample with an ion beam; an electron beam column configured to irradiate the sample with an electron beam; a secondary electron detector configured to detect a secondary electron generated from the sample; an Energy Dispersive X-ray Spectrometry (EDS) detector configured to detect an X-ray generated from the sample; and a control unit configured to change an irradiation condition of the ion beam in a case where an X-ray of a specified material is detected by the EDS detector during a cross-section processing and observation process, the cross-section processing and observation process including: a cross-section processing step of forming a cross-section by irradiating the sample with the ion beam, a cross-section observation step of obtaining an observation image of the cross-section based on the secondary electron or the X-ray generated from the cross-section by irradiating the cross-section with the electron beam; and repeating the cross-section processing step and the cross-section observation step so as to obtain observation images of the plurality of cross-sections formed substantially parallel with each other at predetermined intervals.

According to another aspect of the present invention, there is provided a cross-section processing and observation apparatus including: a sample stage configured to place a sample thereon; an ion beam column configured to irradiate the sample with an ion beam; an electron beam column configured to irradiate the sample with an electron beam; a secondary electron detector configured to detect a secondary electron generated from the sample; an Energy Dispersive X-ray Spectrometry (EDS) detector configured to detect an X-ray generated from the sample; and a control unit configured to change an irradiation condition of the ion beam in a case where an X-ray of an unspecified material other than a material which is specified in advance is detected by the EDS detector during a cross-section processing and observation process, the cross-section processing and observation process including: a cross-section processing step of forming a cross-section by irradiating the sample with the ion beam, a cross-section observation step of obtaining an observation image of the cross-section based on the secondary electron or the X-ray generated from the cross-section by irradiating the cross-section with the electron beam; and repeating the cross-section processing step and the cross-section observation step so as to obtain observation images of the plurality of cross-sections formed substantially parallel with each other at predetermined intervals.

According to the cross-section processing and observation method of the present invention, even for the sample including a minute observation target, it is possible to efficiently obtain observation images of a plurality of cross-sections and to analyze the sample.

DETAILED DESCRIPTION

Hereinafter, embodiments of a cross-section processing and observation method and a cross-section processing and observation apparatus according to the present invention will be described. The cross-section processing and observation apparatus of the embodiment includes a control unit which changes a condition of the cross-section processing and observation in a case where a material of a cross-section, which is based on an X-ray obtained by performing Energy Dispersive X-ray Spectrometry (EDS) measurement during the cross-section processing and observation, and a material of a observation target which is stored in advance coincide with each other. Accordingly, cross-section-processing conditions such as a slice width of the cross-section processing and observation are changed to conditions for performing the cross-section processing and observation of a minute observation target, and the cross-section processing and observation of the minute observation target is performed.

Figure 1:
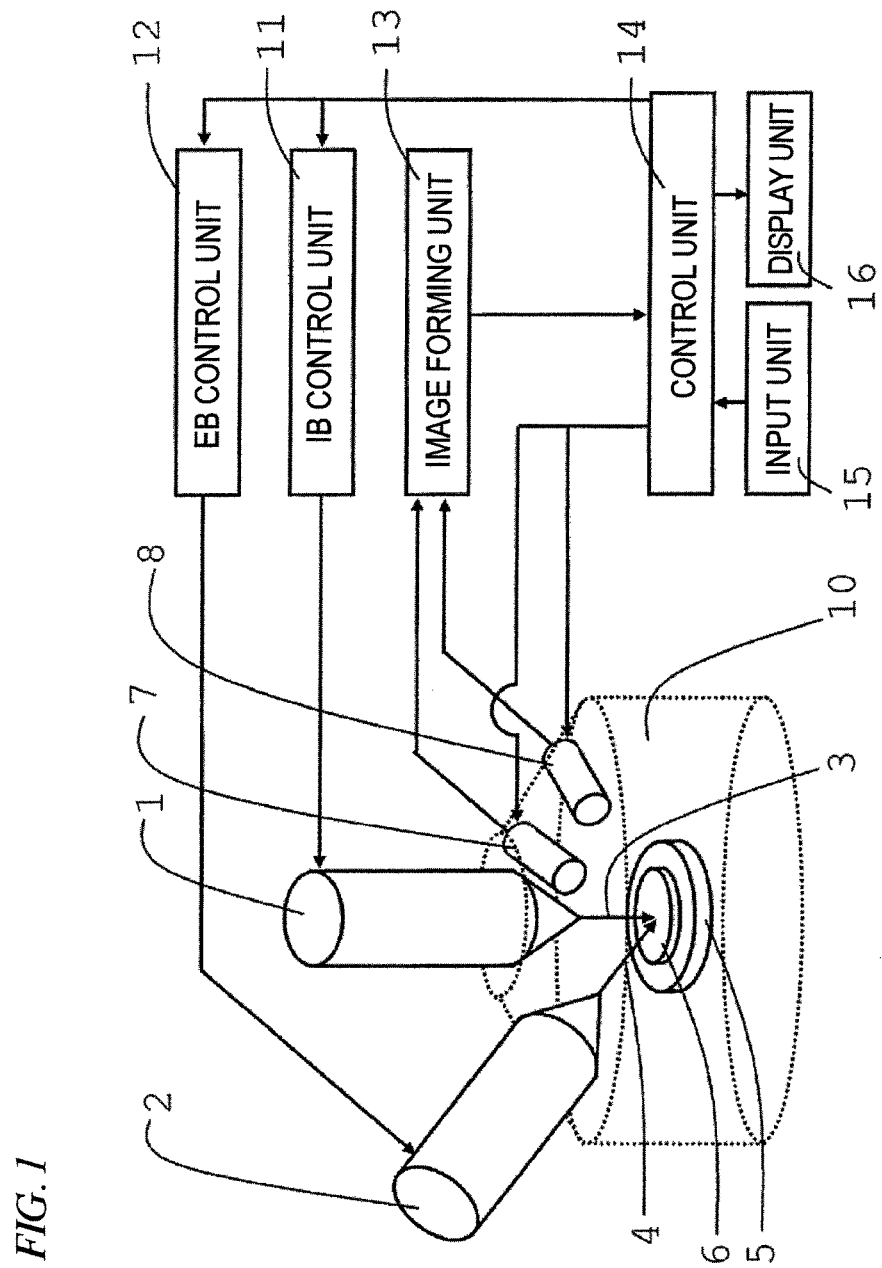
FIG. 1 is a configuration diagram of a cross-section processing and observation apparatus of an embodiment of the present invention.

As shown in FIG. 1, the cross-section processing and observation apparatus includes an ion beam column 1, an electron beam column 2, and a sample chamber 10. The ion beam column 1 and the electron beam column 2 are disposed so as to irradiate the same position on a sample 6 which is placed on a sample stage 5 accommodated in the sample chamber 10 with an ion beam 3 and an electron beam 4. The sample stage 5 can be moved, inclined, and rotated in XYZ directions, and a position of the sample 6 can be adjusted with respect to each beam.

The cross-section processing and observation apparatus includes an ion beam control unit 11 and an electron beam control unit 12. The ion beam control unit 11 transmits an irradiation signal to the ion beam column 1 and emits the ion beam 3 from the ion beam column 1. The electron beam control unit 12 transmits an irradiation signal to the electron beam column 2 and emits the electron beam 4 from the electron beam column 2.

The cross-section processing and observation apparatus further includes a secondary electron detector 7 and an EDS detector 8. The secondary electron detector 7 irradiates the sample 6 with the ion beam 3 or the electron beam 4, and detects secondary electrons generated from the sample 6. In addition, the EDS detector 8 irradiates the sample 6 with the electron beam 4, and detects an X-ray generated from the sample 6.

The cross-section processing and observation apparatus includes an image forming unit 13 which forms an observation image and a display unit 16 which displays the observation image. The image forming unit 13 forms a Scanning Ion Microscope (SIM) image from a signal for scanning the ion beam 3 and a signal of the secondary electrons detected by the secondary electron detector 7. The display unit 16 can display the SIM image. In addition, the image forming unit 13 forms a Scanning Electron Microscope (SEM) image from a signal for scanning the electron beam 4 and the signal of the secondary electrons detected by the secondary electron detector 7. The display unit 16 can display the SEM image. In addition, the image forming unit 13 forms an EDS map from the signal for scanning the electron beam 4 and a signal of the X-ray detected by the EDS detector 8. The display unit 16 can display the EDS map. Herein, the EDS map specifies a material of the sample 6 at an irradiation point of each electron beam from energy of the detected X-ray, and shows distribution of material in an irradiation region of the electron beam 4.

In addition, the cross-section processing and observation apparatus includes a control unit 14 and an input unit 15. An operator inputs conditions related to apparatus control to the input unit 15. The input unit 15 transmits the input information to the control unit 14. The control unit 14 transmits control signals to the ion beam control unit 11, the electron beam control unit 12, and the image forming unit 13, and controls the cross-section processing and observation apparatus.

Figure 2:
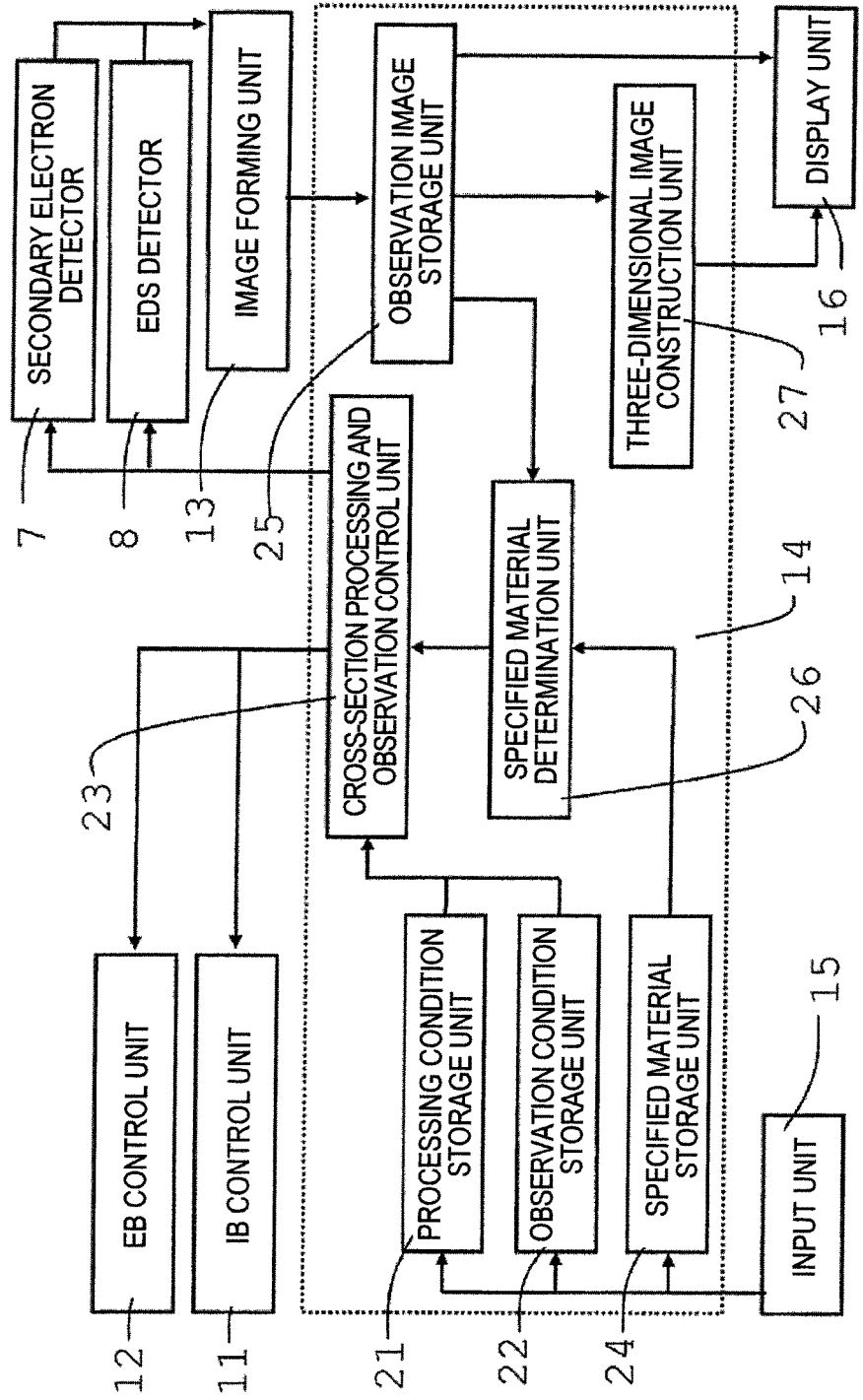
FIG. 2 is a configuration diagram of a control unit of a cross-section processing and observation apparatus of an embodiment of the present invention.

Next, the control unit 14 will be described with reference to FIG. 2. The control unit 14 includes a processing condition storage unit 21, an observation condition storage unit 22, cross-section processing and observation control unit 23, specified material storage unit 24, an observation image storage unit 25, a specified material determination unit 26, and a three-dimensional image construction unit 27.

The processing condition storage unit 21 stores set values of intervals of slice processing, and a position and a size of a processing region of the ion beam 3. The processing condition storage unit 21 stores set values of intervals of slice processing and a size of the processing region for slice processing for finding a large observation target or a minute observation target, and set values of intervals of slice processing and a size of the processing region for analysis of the minute observation target. In addition, the processing condition storage unit 21 stores set values of an accelerating voltage of the ion beam 3, and an amount of current. When using the ion beam 3 which is accelerated with a low accelerating voltage, it is possible to make a damage layer formed on the sample to be smaller, and when using the ion beam 3 having a small amount of current, a beam shape does not spread widely, and accordingly it is preferable in a case of processing the minute observation target since a steep cross-section can be formed. Therefore, the processing condition storage unit 21 stores set values of a high accelerating voltage and a large amount of current for slice processing for finding out the large observation target and the minute observation target, and set values of a low accelerating voltage and a small amount of current for analysis of the minute observation target.

The observation condition storage unit 22 stores set values of a position and a size of the observation region, an accelerating voltage of the electron beam 4, and an amount of current. When using the electron beam 4 which is accelerated with a low accelerating voltage, since a penetration length of the electron beam is small, it is possible to obtain an observation image obtained by reflecting information in the vicinity of the cross-section only, and when using the ion beam 3 having a small amount of current, beam shape does not spread widely, and accordingly, it is preferable in a case of observing the minute observation target since an observation image having high resolution can be obtained. However, if the accelerating voltage is high, since the penetrating length of the electron beam is large, it is possible to obtain an observation image to which the information in the sample is reflected and the minute observation target can be easily found. Accordingly, the observation condition storage unit 22 stores set values of a high accelerating voltage and a large amount of current for cross-section observation for finding a large observation target or a minute observation target, and set values of a low accelerating voltage and a small amount of current for analysis of the minute observation target.

In addition, the observation condition storage unit 22 stores types of observation images. The types of the observation images include the SEM image, the SIM image, and the EDS image. In a case of obtaining the SEM image and the SIM image, the secondary electron is detected by the secondary electron detector 7, and the SEM image and the SIM image are formed by the image forming unit 13. In a case of obtaining the EDS image, the X-ray is detected by the EDS detector 8, and the EDS map is formed by the image forming unit 13.

The specified material storage unit 24 stores an element of the material of the desirable observation target (specified material). In a case where the element is measured by the EDS measurement in the cross-section processing and observation for finding out the minute observation target, the conditions of the cross-section processing and observation are changed.

If an operator inputs the set values and the element from the input unit 15, the cross-section processing and observation apparatus stores the set values and the element to each storage unit. The stored set values of the processing conditions and the observation conditions are read out by the cross-section processing and observation control unit 23. In addition, the element is read out by the specified material determination unit 26.

The cross-section processing and observation control unit 23 transmits the irradiation conditions of the ion beam 3, that is, the processing conditions to the ion beam column 1, and irradiates the sample 6 with the ion beam 3 from the ion beam column 1 to process the sample 6. The cross-section processing and observation control unit 23 transmits the irradiation conditions of the electron beam 4, that is, the observation conditions, to the electron beam column 2, and irradiates the sample 6 with the electron beam 4 from the electron beam column 2 to obtain an observation image of the sample 6 from the secondary electron or the X-ray generated from the sample 6.

The cross-section processing and observation control unit 23 controls the secondary electron detector 7 or the EDS detector 8 depending on the types of the obtained observation images so as to detect the secondary electron or the X-ray. The observation image is formed by the image forming unit 13, based on the detected secondary electron or X-ray.

The observation image storage unit 25 stores the formed observation image. The display unit 16 displays the observation image stored in the observation image storage unit 25. In a case of constructing a three-dimensional image which will be described later, the three-dimensional image construction unit 27 reads out the observation image stored in the observation image storage unit 25, and constructs a three-dimensional image. The display unit 16 displays the constructed three-dimensional image.

The specified material determination unit 26 reads out from the specified material storage unit 24 the element of the material which is stored in advance (specified material), in the execution of the cross-section processing and observation, and reads out from the observation image storage unit 25 the EDS map obtained by the cross-section processing and observation. In a case where the element appears in the EDS map, the specified material determination unit 26 transmits a signal to the cross-section processing and observation control unit 23. The cross-section processing and observation control unit 23 receives the signal and changes the irradiation conditions, which will be described later.

Figure 3A:
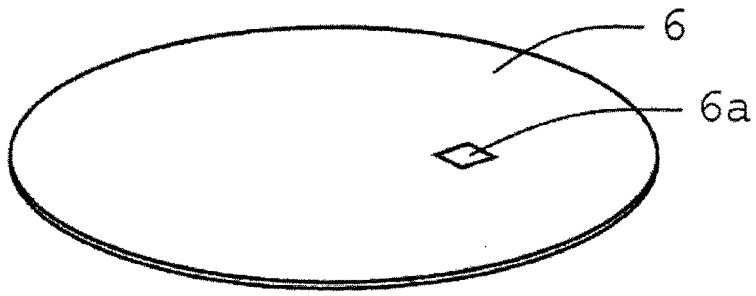
FIG. 3A is an explanatory diagram of a sample of an embodiment of the present invention.

Next, the cross-section processing and observation will be described with reference to FIG. 3. FIG. 3A is a diagram showing the sample 6 which is a semiconductor wafer, and the sample 6 has a minute device structure therein. In the cross-section processing and observation, the cross-section observation image of the desirable observation target such as the device structure or defect in the sample 6 is obtained and analyzed. In a case of the minute observation target, it is difficult to accurately grasp the position of the observation target existing in the sample 6 due to positioning accuracy of the sample stage or accuracy of the device manufacturing. Herein, the ion beam 3 is emitted in the vicinity of the position in which it is considered that the observation target exists, a processing groove 6a is formed by etching process, and a processing region of the cross-section processing is set so as to gradually widen the processing groove 6a towards the position in which it is considered that the observation target exists.

Figure 3B:
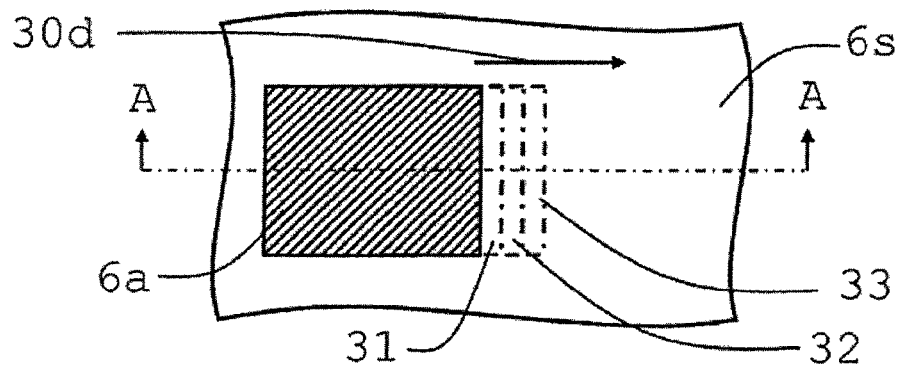
FIGS. 3B and 3C are explanatory diagrams of a cross-section processing and observation of an embodiment of the present invention.
Figure 3C:
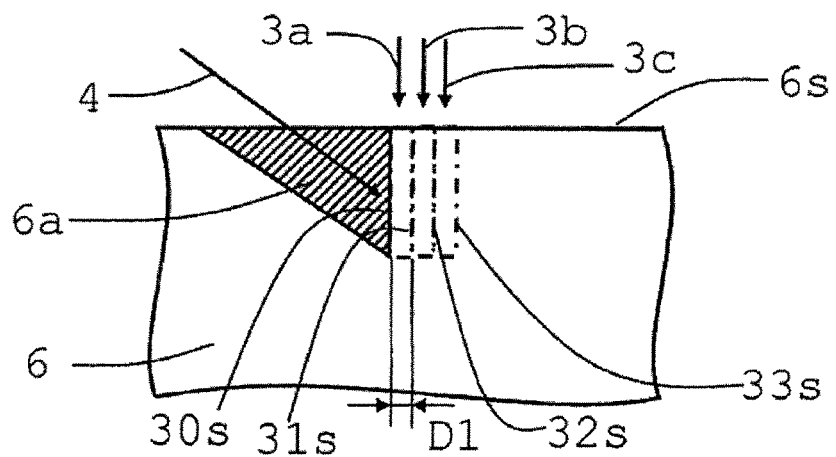

FIG. 3B is an enlarged diagram of the vicinity of the processing groove 6a and FIG. 3C is a cross-sectional view taken along line A-A of FIG. 3B. The processing groove 6a has a slope shape so that a cross-section 30s can be irradiated with the electron beam 4. Processing regions 31, 32, and 33 of slice processing are set so as to widen the processing groove 6a from the cross-section 30s in a processing direction 30d. Slice intervals D1 of the slice processing of the processing regions 31, 32, and 33 are constant.

Next, the cross-section processing and the cross-section observation are started. The processing region 31 is subjected to etching processing by an ion beam 3a, and an exposed cross-section 31s is irradiated with the electron beam 4, to obtain an observation image of the cross-section 31s. Next, the processing region 32 is subjected to etching processing by an ion beam 3b, and an exposed cross-section 32s is irradiated with the electron beam 4, to obtain an observation image of the cross-section 32s. Next, the processing region 33 is subjected to etching processing by an ion beam 3c, and an exposed cross-section 33s is irradiated with the electron beam 4, to obtain an observation image of the cross-section 33s. As described above, the cross-section processing and the cross-section observation are repeatedly performed to obtain the observation images of the plurality of cross-sections.

Next, in the cross-section processing and observation, an embodiment of performing the cross-section processing and observation for the minute observation target and constructing the three-dimensional image of the observation target, and an embodiment of automatically performing the cross-section processing and observation of the sample including the minute observation target will be described.

Embodiment 1

An embodiment of the cross-section processing and observation method of constructing the three-dimensional image from the plurality of obtained observation images will be described.

Figure 4:
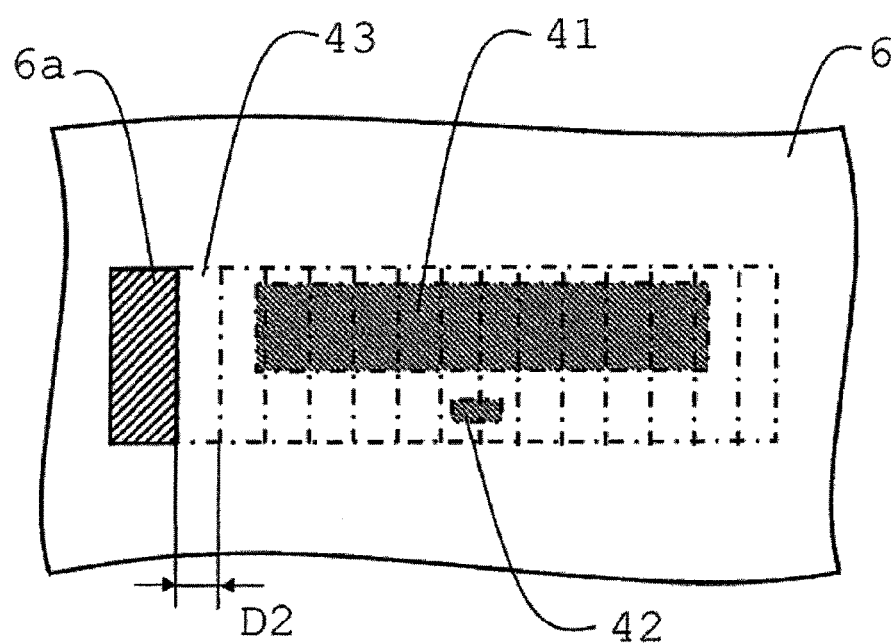
FIG. 4 is an explanatory diagram of cross-section processing and observation of an embodiment of the present invention.

FIG. 4 is a diagram showing the sample 6 including a defect which is the minute observation target. The sample 6 also includes a structure 41 of the device larger than the defect 42. The cross-section processing and observation of the sample 6 is performed for analyzing the defect 42.

First, the processing groove 6a is formed in a vicinity of the position in which it is considered that the defect 42 exists, by the etching processing using the ion beam 3. Next, the condition setting of the cross-section processing and observation is performed.

In the condition setting, as the processing conditions for finding out the defect 42, a position and a size of a first processing region 43 are set by setting a slice interval D2 of the slice processing to 50 nm. In addition, as the observation conditions, an accelerating voltage of the electron beam 4 is set to 5 kV. Carbon or iron is set as the element of the material of the observation target.

If the cross-section observation is performed with the electron beam 4 accelerated with the accelerating voltage of 5 kV, a penetrating length of the electron beam into the sample 6 is approximately 50 nm. Herein, if the cross-section is irradiated with the electron beam 4 by setting the slice interval D2 to 50 nm, since the electron beam 4 is incident thereto in the next range to be subjected to slice processing, that is, the range of the slice interval D2, the X-ray of the defect 42 can be detected in a case where the defect exists in this range. Accordingly, even when the size of the defect 42 is equal to or smaller than the slice interval of 50 nm, it is possible to find the defect 42 in the cross-section processing and observation at the slice interval of 50 nm.

In addition, as the processing conditions for performing cross-section processing and observation of the defect 42, the slice interval of the slice processing is set to 5 nm. Therefore, a plurality of cross-sections can be formed with respect to the defect 42.

Next, the cross-section processing and observation for finding out the defect 42 is started. The first processing region 43 is irradiated with the ion beam 3, and the slice processing is performed. Then, the cross-section formed in the slice processing is irradiated with the electron beam 4, and the generated X-ray is detected by the EDS detector 8. At that time, the X-ray of silicon, oxygen, aluminum, copper, or the like which is the material configuring the device is detected from the sample 6 which is the semiconductor device. The image forming unit 13 forms the EDS map which shows distribution of the material of the irradiation region of the electron beam 4, based on the irradiation position of the electron beam 4 and the detected X-ray. The slice processing and the EDS map formation are repeatedly performed.

In a case where carbon or iron which is the material of the defect 42 appears in the EDS map, the cross-section processing and observation control unit 23 reads out the processing conditions for cross-section processing and observation of the defect 42, and changes the processing conditions.

Figure 5A:
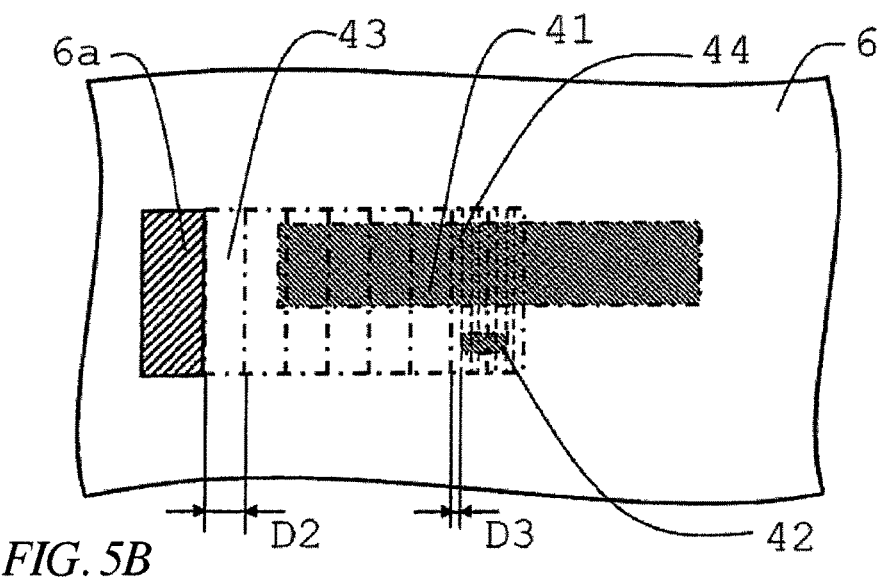
FIGS. 5A and 5B are explanatory diagrams of cross-section processing and observation of an embodiment of the present invention.
Figure 5B:
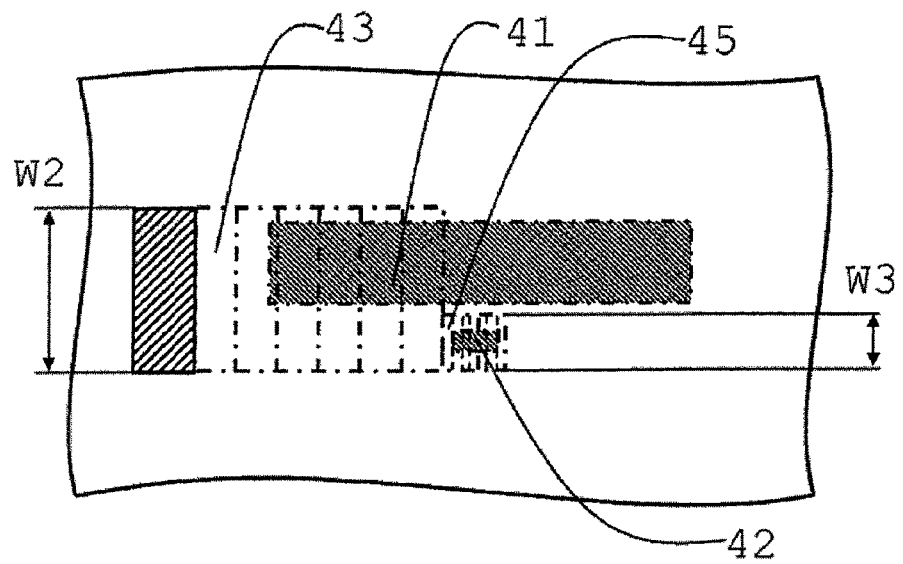

In the changing of the processing conditions, the interval is changed to a slice interval D3 of 5 nm as shown in FIG. 5A. In addition, as the observation conditions, the X-ray is detected by the EDS detector 8 hereinabove. However, hereinafter the conditions are changed to the conditions for detecting the secondary electron by the secondary electron detector 7, and forming the SEM image by the image forming unit 13. The cross-section processing and observation of the defect 42 is performed with the conditions.

A second processing region 44 is irradiated with the ion beam 3, the slice processing is performed, and the SEM image of the formed cross-section is obtained. Accordingly, even when a length of the defect 42 in the processing direction is approximately 60 nm, since the slice processing is performed at the slice interval of 5 nm, approximately 12 SEM images can be obtained, and therefore it is possible to sufficiently analyze the defect 42.

Next, as the processing conditions for cross-section processing and observation of the defect 42, it is preferable to have a small size of the processing region and to shorten the processing time. The position of the defect 42 is confirmed from the EDS map in which the X-ray of the defect 42 is detected in the cross-section processing and observation for finding out the defect 42. A processing region for slice process of only the vicinity of the position, in which the defect 42 exists, is set.

As shown in FIG. 53, a third processing region 45 for cross-section processing and observation of the defect 42 is set. Since a processing width W3 of the third processing region 45 is smaller than a processing width W2 of the first processing region 43, the processing area can be further miniaturized, and time for processing can be shortened.

Next, the three-dimensional image is constructed from the observation image obtained in the cross-section processing and observation, by the three-dimensional image construction unit 27. The three-dimensional image construction unit 27 constructs the three-dimensional image by arranging the plurality of observation images stored in the observation image storage unit 25, in an obtained order, at the intervals corresponding to the slice intervals, to be substantially parallel with each other. Accordingly, since the slice interval is adjusted according to the observation target and the observation image is obtained, it is possible to construct the three-dimensional image in which even the minute defect 42 is three-dimensionally displayed. Therefore, even the sample including the minute defect can be analyzed by the three-dimensional image.

Embodiment 2

Figure 6:
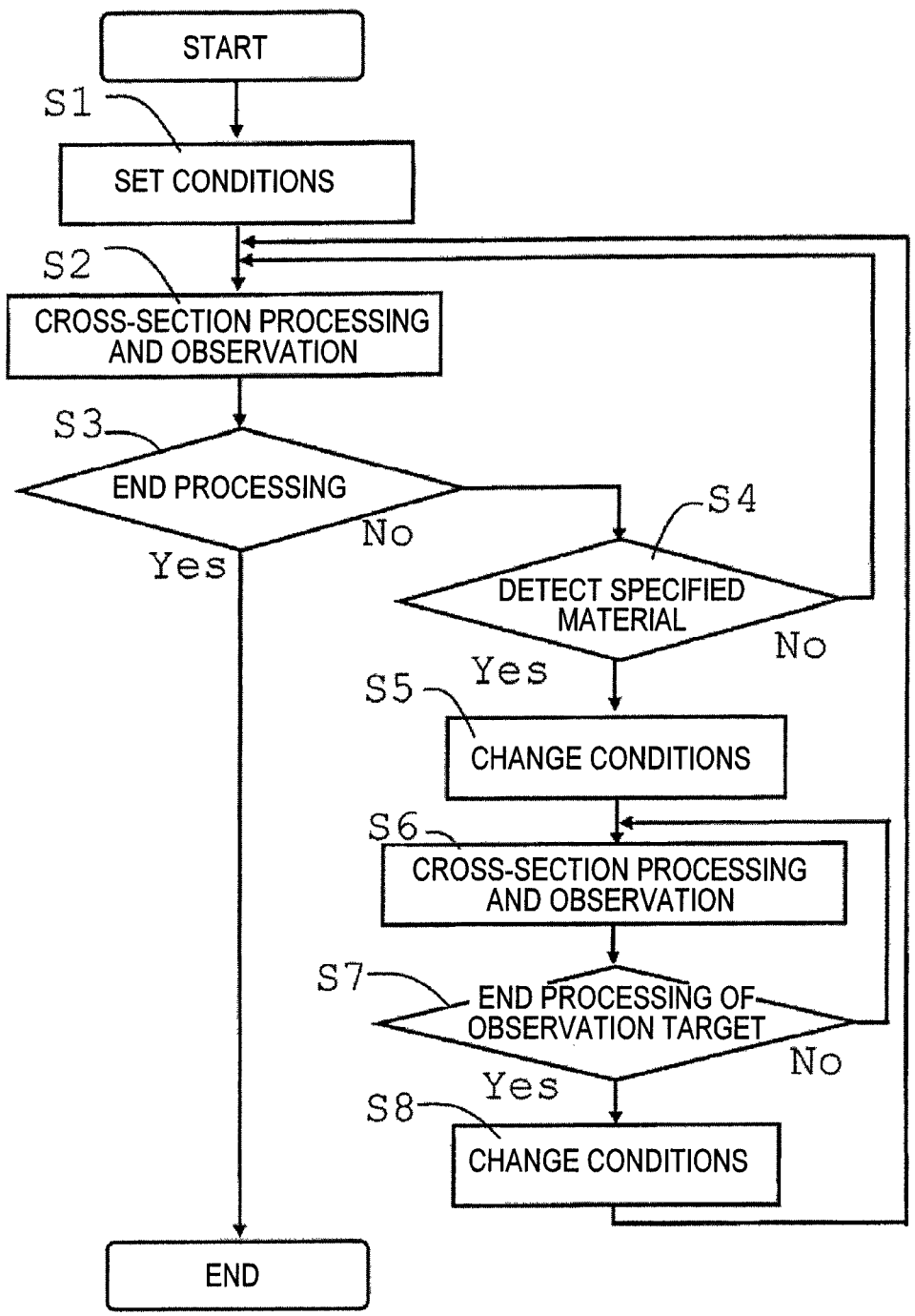
FIG. 6 is a flowchart of an embodiment of the present invention.
Figure 7:
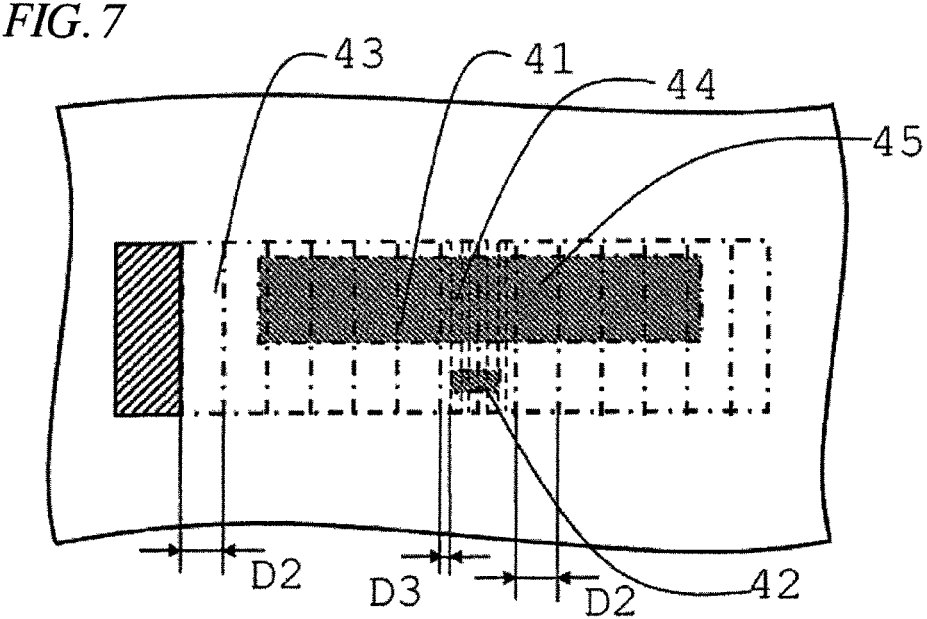
FIG. 7 is an explanatory diagram of cross-section processing and observation of an embodiment of the present invention.

An embodiment of the cross-section processing and observation method of automatically performing the cross-section processing and observation of the sample including the minute observation target will be described. FIG. 6 is a flowchart of the cross-section processing and observation method. FIG. 7 is a diagram showing the sample 6 including the defect 42 which is the minute observation target.

First, the condition setting of the cross-section processing and observation is performed (S1). In the condition setting, as the processing and observation conditions for finding out the defect 42, the position and the size of the first processing region 43 are set, by setting the slice interval D2 of the slice processing to 50 nm. In addition, as the observation conditions, an accelerating voltage of the electron beam 4 is set to 5 kV. Carbon or iron is set as the element of the material of the observation target. In addition, as the processing conditions of the defect 42, the slice interval of the slice processing is set to 5 nm. As the observation conditions of the defect 42, an accelerating voltage of the electron beam 4 is set to 1 kV.

Next, cross-section processing and observation is performed (S2). The first processing region 43 is irradiated with the ion beam 3, and the slice processing is performed. Then, the cross-section formed in the slice processing is irradiated with the electron beam 4, and the generated X-ray is detected by the EDS detector 8. At that time, the X-ray of silicon, oxygen, aluminum, copper, or the like which is the material configuring the device is detected from the sample 6 which is the semiconductor device. The image forming unit 13 forms the EDS map which shows distribution of the material of the irradiation region of the electron beam 4, based on the irradiation position of the electron beam 4 and the detected X-ray. The slice processing and the EDS map formation are repeatedly performed. When reaching the predetermined number of slice processing or the number of obtained observation images, the processing ends (S3).

When carbon or iron which is the material of the defect 42 appears in the EDS map in performing the cross-section processing and observation (S4), the cross-section processing and observation control unit 23 reads out the processing and observation conditions of the defect 42 and changes the conditions (S5). The example of FIG. 7 corresponds to the change of the slice interval of the slice processing from D2 (=50 nm) to D3 (=5 nm).

Next, with the processing and observation conditions of the defect 42, in the second processing region 44, the cross-section processing and observation is performed while forming the cross-section (S6). In a case where the cross-section processing and observation of the defect 42 is performed and the defect 42 is removed from the obtained observation image or the EDS map, that is, in a case where the slice processing of the defect 42 is ended (S7), the condition changing is performed again (S8). The example of FIG. 7 corresponds to the change of the slice interval of the slice processing from D3 (=5 nm) to D2 (=50 nm). The condition changing is a change of returning the conditions to the processing and observation conditions for finding out the defect 42, and the cross-section processing and observation (S2) is started again for finding out a new defect. That is, while performing the slice processing of the third processing region 45, the new defect is searched for. Then, when reaching the predetermined number of slice processing or the number of obtained observation images, the processing ends (S3).

By automatically performing the processes described above by the cross-section processing and observation apparatus, the slice interval can be automatically changed even for the sample including the minute observation target, and therefore, it is possible to efficiently and accurately obtain the desirable observation image.

Embodiment 3

Instead of the cross-section processing and observation apparatus described above, an embodiment of performing the cross-section processing and observation method using a cross-section processing and observation apparatus, in which irradiation axes of the ion beam column 1 and of the electron beam column 2 orthogonal to each other, will be described.

Figure 8:
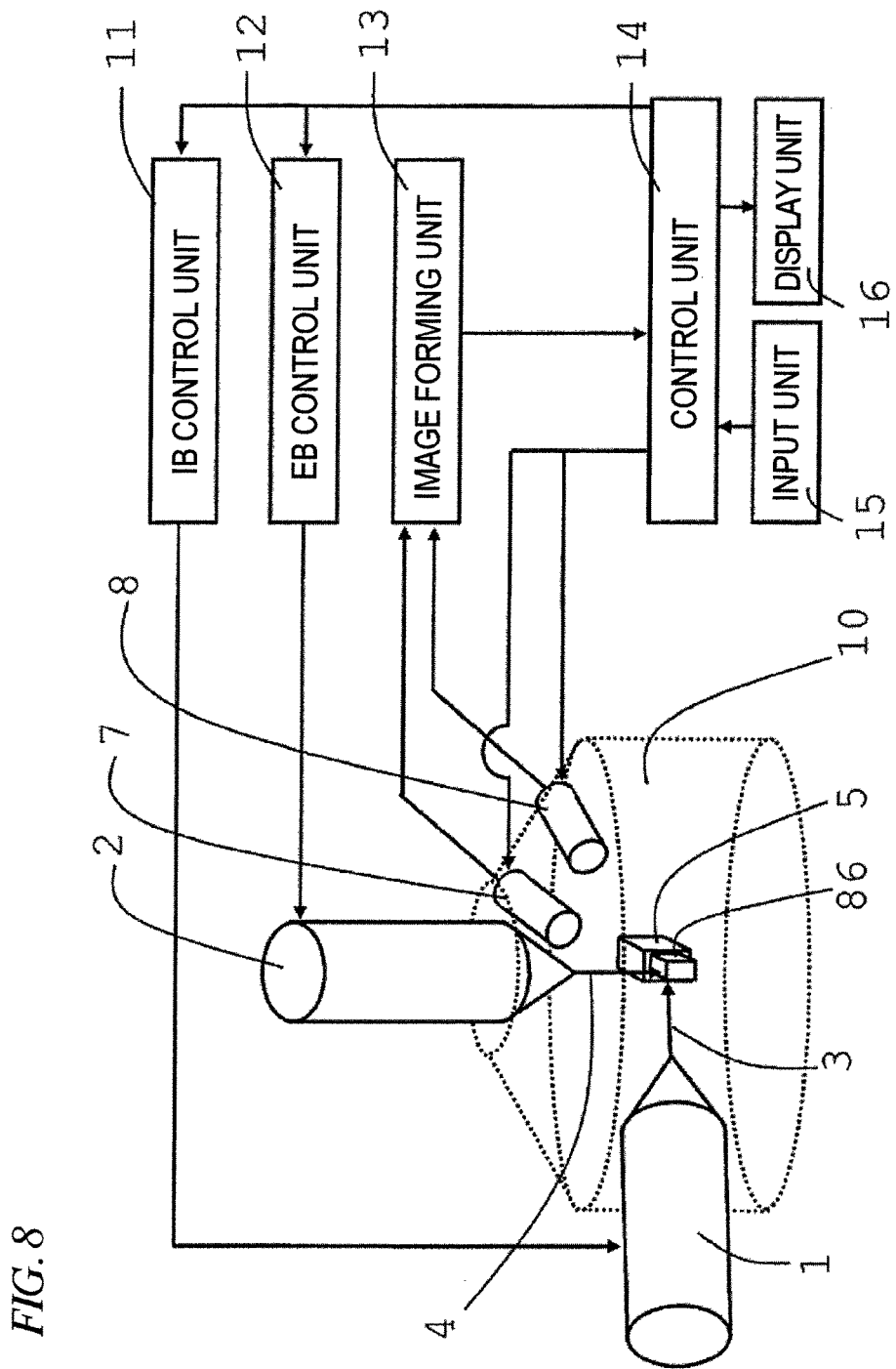
FIG. 8 is a configuration diagram of a cross-section processing and observation apparatus of an embodiment of the present invention.

As shown in FIG. 8, the ion beam column 1 and the electron beam column 2 are disposed so that the irradiation axes are orthogonal to each other. Accordingly, without changing a direction of a small piece sample 86, the electron beam 4 can be vertically incident with respect to the cross-section which is processed and exposed by the ion beam 3. Regarding the obtaining of the observation image, it is possible to obtain the observation image with high resolution, when irradiating an observation surface with the electron beam from the orthogonal direction, compared to a case of irradiating from the inclined direction. Therefore, by setting such an apparatus configuration, it is possible to obtain the observation image with high resolution in the cross-section processing and observation.

Figure 9A:
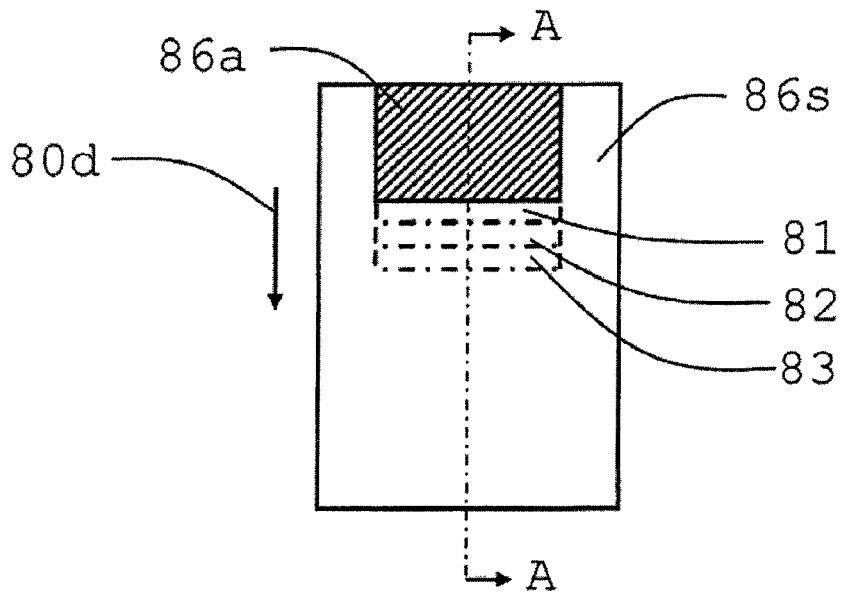
FIGS. 9A and 9B are explanatory diagrams of cross-section processing and observation of an embodiment of the present invention.
Figure 9B:
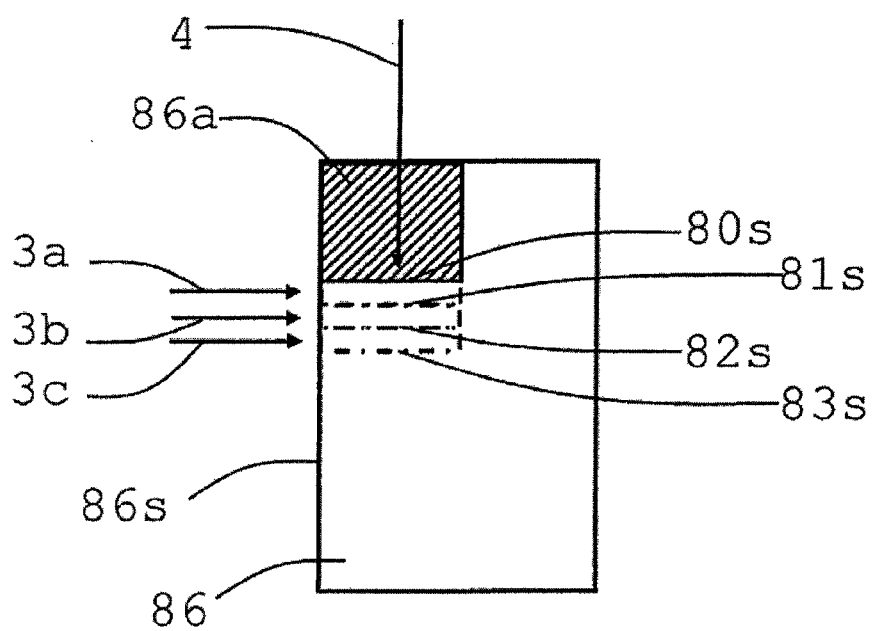

FIG. 9A is a surface diagram of the small piece sample 86 and FIG. 9B is a cross-sectional view taken along line A-A of FIG. 9A. A processing groove 86a is formed by the etching process performed by the ion beam 4 on an end portion of the small piece sample 86, so that the electron beam 4 can be orthogonally incident to the cross-section 30s. Then, processing regions 81, 82, and 83 of the cross-section processing are set so as to widen the processing groove 86a towards the position in which it is considered that the observation target exists.

The processing region 81 is subjected to etching processing by an ion beam 3a, and an exposed cross-section 81s is irradiated with the electron beam 4, to obtain an observation image of the cross-section 81s. Since the electron beam 4 is orthogonally incident with respect to the cross-section 81s, it is possible to obtain the observation image with high resolution. Next, the processing region 82 is subjected to etching processing by an ion beam 3b, and an exposed cross-section 82s is irradiated with the electron beam 4, to obtain an observation image of the cross-section 82s. Next, the processing region 83 is subjected to etching processing by an ion beam 3c, and an exposed cross-section 83s is irradiated with the electron beam 4, to obtain an observation image of the cross-section 83s. As described above, the cross-section processing and the cross-section observation are repeatedly performed to obtain the observation images of the plurality of cross-sections.

By performing the cross-section processing and observation method described above using the cross-section processing and observation apparatus of the embodiment, it is possible to obtain the observation image with higher resolution and to perform more specific analysis compared to the case where the electron beam 4 is obliquely incident to the observation surface.

Embodiment 4

In the embodiments described above, during the execution of the cross-section processing and observation, the specified material determination unit 26 reads out the element of the material which is stored in advance (specified material) from the specified material storage unit 24, and reads out the EDS map obtained by the cross-section processing and observation from the observation image storage unit 25. In a case where the element appears in the EDS map, the specified material determination unit 26 transmits the signal to the cross-section processing and observation control unit 23. That is, in the embodiments 1 to 3, an operator grasps in advance the element to be detected and the embodiments are suitably used in the cross-section processing and observation method at the time of detecting the element which is grasped in advance.

In contrast, in a case of, for example, a general mineral which is different from a device artificially manufactured such as the semiconductor device, in many cases, it is not clear which element is included as a defect in addition to a base material. In such a case, it is considered that the defect or the like of the mineral can be easily detected in many cases by detecting the element other than the base material which is grasped in advance, for example. Hereinafter, an object of the embodiment is to determine existence of an unspecified material (defect or the like) other than the material which is specified in advance (specified material), and to efficiently perform the cross-section processing and observation.

In the same manner as the embodiments 1 to 3, an operator inputs the specified element to the input unit 15. However, the element input herein is an element for which an operator does not desire aggressive detection and desires to remove from the detection target. For example, an element which is grasped in advance to exist as the base material of the sample 6 and which is not desired for specific observation is exemplified. Of course, the method of selecting the element to be removed from the detection target depends on conditions.

The specified material determination unit 26 reads out the element of the material which is input from the input unit 15 and is stored in advance, from the specified material storage unit'24, in the execution of the cross-section processing and observation, and reads out the EDS map obtained by the cross-section processing and observation, from the observation image storage unit 25.

In this embodiment, in a case where the unspecified material other than the material stored in the specified material storage unit 24 appears in the EDS map, the specified material determination unit 26 transmits a signal to the cross-section processing and observation control unit 23. The cross-section processing and observation control unit 23 receives the signal and changes the irradiation conditions which are the same as those described in the examples 1 to 3. In the example, since the specified material determination unit 26 determines the unspecified material other than the specified material which is specified by the operator through the input unit 15, the specified material determination unit can be also called an unspecified material determination unit.

Figure 10:
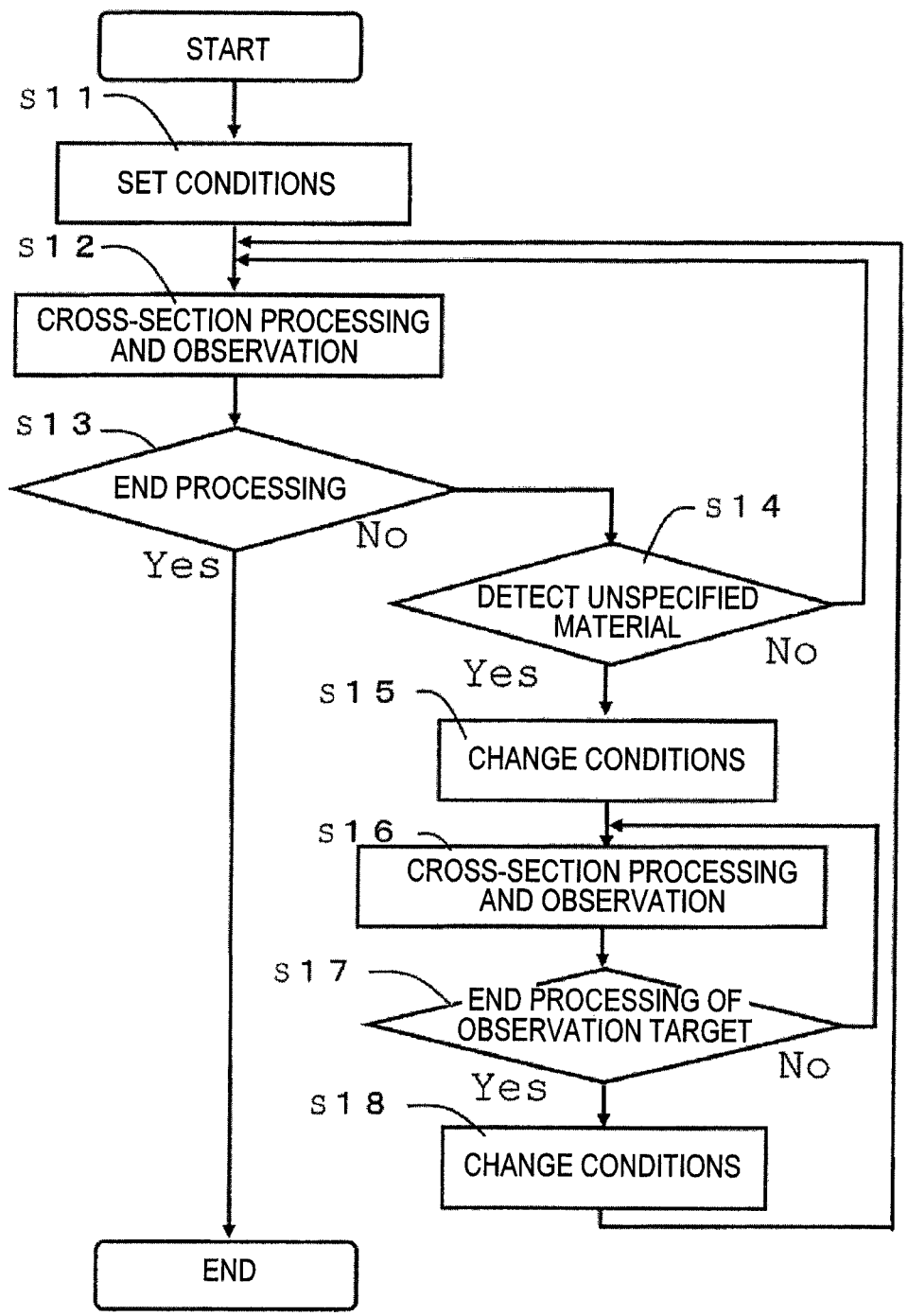
FIG. 10 is a flowchart of an embodiment of the present invention.
Figure 11:
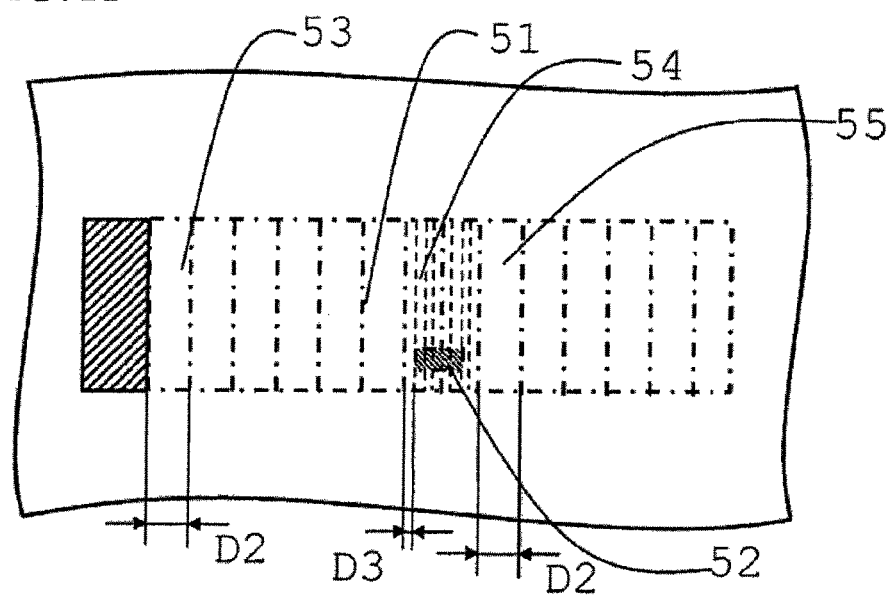
FIG. 11 is explanatory diagram of cross-section processing and observation of an embodiment of the present invention.

FIG. 10 is a flowchart of the cross-section processing and observation method of the embodiment 4. FIG. 11 is a diagram showing the sample 6 including an unspecified material 52 (for example, defect) which is the minute observation target.

First, the condition setting of the cross-section processing and observation is performed (S11). In the condition setting, as the processing and observation conditions, a position and a size of a first processing region 53 are set by setting the slice interval D2 of the slice processing to 50 nm. In addition, as the observation conditions, an accelerating voltage of the electron beam 4 is set to 5 kV. As the element of the specified material, at least one element of the base material 51 of the sample 6 which is specified in advance, for example, is set, and is input from the input unit 15. In addition, as the processing conditions of the case where the unspecified material 52 other than the element of the base material 51 appears, the slice interval of the slice processing is set to 5 nm. As the observation conditions of the unspecified material 52, an accelerating voltage of the electron beam 4 is set to 1 kV.

Next, cross-section processing and observation is performed (S12). The first processing region 53 is irradiated with the ion beam 3, and the slice processing is performed. Then, the cross-section formed in the slice processing is irradiated with the electron beam 4, and the generated X-ray is detected by the EDS detector 8. At this time, the X-ray of the element of the base material 51 such as iron, oxygen, aluminum, copper, or the like which is the material configuring the mineral is detected from the sample 6 which is the mineral directly sampled from a mine, for example. The image forming unit 13 forms the EDS map which shows distribution of the material of the irradiation region of the electron beam 4, based on the irradiation position of the electron beam 4 and the detected X-ray. The slice processing and the EDS map formation are repeatedly performed. When reaching the predetermined number of slice processing or the number of obtained observation images, the processing ends (S13).

When the unspecified material 52 other than the element of the base material 51 appears in the EDS map, in the execution of the cross-section processing and observation (S14), the cross-section processing and observation control unit 23 reads out the processing and observation conditions of the unspecified material 52 and changes the conditions (S15). The example of FIG. 11 corresponds to the change of the slice interval of the slice processing from D2 (=50 nm) to D3 (=5 nm).

Next, with the processing and observation conditions of the unspecified material 52, in a second processing region 54, the cross-section processing and observation is performed while forming the cross-section (S16). In a case where the cross-section processing and observation of the unspecified material 52 is performed and the unspecified material 52 is disappeared from the obtained observation image or the EDS map, that is, in a case where the slice processing of the unspecified material 52 is ended (S17), the condition changing is performed again (S18). The example of FIG. 11 corresponds to the change of the slice interval of the slice processing from D3 (=5 nm) to D2 (=50 nm). The condition changing is the change of returning the conditions to the processing and observation conditions for finding out the unspecified material 52, and the cross-section processing and observation (S12) is started again for finding out new unspecified material. That is, while performing the slice processing of a third processing region 55, the new unspecified material is searched for. Then, when reaching the predetermined number of slice processing or the number of obtained observation images, the processing ends (S13).

By automatically performing the processes described above by the cross-section processing and observation apparatus, the slice interval can be automatically changed even for the sample including the minute observation target, and therefore, it is possible to efficiently and accurately obtain the desirable observation image.

In the above described embodiments 1 to 4, when the X-ray of the specified material or the unspecified material is detected, the cross-section processing and observation control unit 23 of the control unit 14 changes the processing conditions. For an operator, this changing operation is an automatic operation performed by the cross-section processing and observation apparatus. However, the present invention is not limited to this automatic changing, and for example, an operator can manually change the processing conditions.

In the above-described embodiments, when the X-ray of the specified material or the unspecified material is detected by the EDS detector 8, the observation image including the specified material or the unspecified material is formed by the image forming unit 13, and the observation image storage unit 25 stores the formed observation image. The display unit 16 displays the observation image stored in the observation image storage unit 25. The specified material determination unit 26 reads out from the observation image storage unit 25 the specified material or the unspecified material and transmits a signal to the cross-section processing and observation control unit 23. The cross-section processing and observation control unit 23 receives the signal and changes the irradiation conditions (processing conditions).

Here, the specified material determination unit 26 may be configured not to transmit the signal to the cross-section processing and observation control unit 23, and instead, transmit the signal to the display unit 16. Then, when the display unit 16 reads out the observation image from the observation image storage unit 25 and displays the observation image, the display unit 16 may simultaneously display information indicating that the X-ray of the specified material or the unspecified material has been detected. The information can be displayed in various ways, for example, by using characters or pictures. Thereby, the operator can know the detection of the X-ray thorough the display unit 16, and the operator can operate the input unit 15 so as to manually change the processing conditions such as the slicing intervals. By this operation, the processing conditions such as set values of the intervals of slice processing and a position and a size of a processing region of the ion beam 3, which are stored in the processing condition storage unit 21, can be changed. Here, the detection of the X-ray can be notified to the operator in a different manner as described above. For example, the notification to the operator may be performed by sound by using a sound source (not shown).

That is, according to the above-described example, the EDS measurement by the EDS detector 8 can be used as a trigger for changing the processing conditions. Accordingly, it becomes possible to change the processing conditions depending on the operator's preference, without being automatically changed by the apparatus.

A program for executing each procedure of the embodiments 1 to 4 described above is stored in the control unit 14. However, the program can also be stored in the other portion of the cross-section processing and observation apparatus. Of course, the cross-section processing and observation apparatus can be controlled by the program through the network.

The present invention is not limited to the embodiments, and modification and improvement can be suitably performed. In addition, the material, the shape, the dimension, the numerical value, the number, the disposition place, and the like of each constituent element of the embodiments described above are arbitrary and not limited, as long as the present invention can be achieved.

What is claimed is:

1. A cross-section processing and observation apparatus comprising:
   a sample stage configured to place a sample thereon;
   an ion beam column configured to irradiate the sample with an ion beam;
   an electron beam column configured to irradiate the sample with an electron beam;
   a secondary electron detector configured to detect secondary electrons generated from the sample;
   an Energy Dispersive X-ray Spectrometry (EDS) detector configured to detect an X-ray generated from the sample; and
   a control unit configured to automatically change an irradiation condition of the ion beam in a case where an X-ray is generated from a defect which exists in a certain predetermined slice interval before a slice processing and is detected by the EDS detector during a slice processing and observation process, the slice processing and observation process including:
      a slice processing step of forming a cross-section by irradiating the sample with the ion beam,
      a cross-section observation step of obtaining an observation image of the cross-section based on the secondary electrons or the X-ray generated from the cross-section by irradiating the cross-section with the electron beam, and
      repeating the slice processing step and the cross-section observation step so as to obtain observation images of the plurality of cross-sections formed substantially parallel with each other at predetermined intervals, wherein
   the control unit is configured to change, as the irradiation condition, the predetermined slice intervals to be smaller, and
   the control unit includes a three-dimensional image construction unit configured to construct a three-dimensional image based on the obtained observation images.

2. The cross-section processing and observation apparatus according to claim 1, wherein the control unit is configured to also change, as the irradiation condition, an irradiation region of the ion beam to be smaller.

3. The cross-section processing and observation apparatus according to claim 1, wherein the control unit is configured to also change, as the irradiation condition, an amount of current of the ion beam to be smaller.

4. A cross-section processing and observation apparatus comprising:
   a sample stage configured to place a sample thereon;
   an ion beam column configured to irradiate the sample with an ion beam;
   an electron beam column configured to irradiate the sample with an electron beam;
   a secondary electron detector configured to detect secondary electrons generated from the sample;
   an Energy Dispersive X-ray Spectrometry (EDS) detector configured to detect an X-ray generated from the sample; and
   a control unit configured to change an irradiation condition of the ion beam to set an irradiation region of the ion beam to be smaller in a case where an X-ray is generated from a defect which exists in a certain predetermined slice interval before a slice processing and is detected by the EDS detector during a slice processing and observation process, the slice processing and observation process including:
      a slice processing step of forming a cross-section by irradiating the sample with the ion beam,
      a cross-section observation step of obtaining an observation image of the cross-section based on the secondary electrons or the X-ray generated from the cross-section by irradiating the cross-section with the electron beam, and
      repeating the slice processing step and the cross-section observation step so as to obtain observation images of the plurality of cross-sections formed substantially parallel with each other at predetermined slice intervals, wherein
   the control unit is configured to also change, as the irradiation condition, the predetermined slice intervals to be smaller, and
   the control unit includes a three-dimensional image construction unit configured to construct a three-dimensional image based on the obtained observation images.

5. The cross-section processing and observation apparatus according to claim 4, wherein the control unit is configured to also change, as the irradiation condition, an amount of current of the ion beam to be smaller.

6. A cross-section processing and observation apparatus comprising:
   a sample stage configured to place a sample thereon;
   an ion beam column configured to irradiate the sample with an ion beam;
   an electron beam column configured to irradiate the sample with an electron beam;
   a secondary electron detector configured to detect secondary electrons generated from the sample;
   an Energy Dispersive X-ray Spectrometry (EDS) detector configured to detect an X-ray generated from the sample; and
   a control unit configured to change an irradiation condition of the ion beam to set an amount of current of the ion beam to be smaller in a case where an X-ray is generated from a defect which exists in a certain predetermined slice interval before a slice processing and is detected by the EDS detector during a slice processing and observation process, the slice processing and observation process including:
      a slice processing step of forming a cross-section by irradiating the sample with the ion beam,
      a cross-section observation step of obtaining an observation image of the cross-section based on the secondary electrons or the X-ray generated from the cross-section by irradiating the cross-section with the electron beam, and
      repeating the slice processing step and the cross-section observation step so as to obtain observation images of the plurality of cross-sections formed substantially parallel with each other at predetermined slice intervals, wherein
   the control unit is configured to also change, as the irradiation condition, the predetermined slice intervals to be smaller, and
   the control unit includes a three-dimensional image construction unit configured to construct a three-dimensional image based on the obtained observation images.

* * * * *